(12) United States Patent
Hill et al.

(10) Patent No.: US 8,747,462 B2
(45) Date of Patent: Jun. 10, 2014

(54) CORKSCREW ANNULOPLASTY DEVICE

(75) Inventors: Jason Hill, Brooklyn Park, MN (US); Mark L. Jenson, Greenfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 143 days.

(21) Appl. No.: 13/241,603

(22) Filed: Sep. 23, 2011

(65) Prior Publication Data
US 2012/0296417 A1 Nov. 22, 2012

Related U.S. Application Data

(60) Provisional application No. 61/487,063, filed on May 17, 2011.

(51) Int. Cl.
*A61F 2/24* (2006.01)

(52) U.S. Cl.
USPC .......................................... 623/2.37

(58) Field of Classification Search
USPC .............................. 623/1.24, 2.36, 2.38, 2.39
See application file for complete search history.

(56) References Cited

U.S. PATENT DOCUMENTS

| | | | |
|---|---|---|---|
| 5,064,431 A | 11/1991 | Gilbertson et al. | |
| 5,441,516 A | 8/1995 | Wang et al. | |
| 5,449,372 A | 9/1995 | Schmaltz et al. | |
| 5,836,968 A | 11/1998 | Simon et al. | |
| 5,855,565 A | 1/1999 | Bar-Cohen et al. | |
| 6,074,418 A * | 6/2000 | Buchanan et al. | 623/2.11 |
| 6,270,515 B1 | 8/2001 | Linden et al. | |
| 6,391,054 B2 | 5/2002 | Carpentier et al. | |
| 6,432,131 B1 | 8/2002 | Ravenscroft | |
| 6,517,584 B1 | 2/2003 | Lecalve | |
| 6,619,291 B2 | 9/2003 | Hlavka et al. | |
| 6,676,702 B2 | 1/2004 | Mathis | |
| 6,682,546 B2 | 1/2004 | Amplatz | |
| 6,689,164 B1 | 2/2004 | Seguin | |
| 6,726,716 B2 | 4/2004 | Marquez | |
| 6,743,219 B1 | 6/2004 | Dwyer et al. | |
| 6,921,407 B2 | 7/2005 | Nguyen et al. | |
| 6,997,951 B2 | 2/2006 | Solem et al. | |
| 7,060,021 B1 | 6/2006 | Wilk | |

(Continued)

FOREIGN PATENT DOCUMENTS

| | | |
|---|---|---|
| DE | 102007043831 A1 | 4/2009 |
| WO | 03/075748 | 9/2003 |

(Continued)

OTHER PUBLICATIONS

Search Report and Written Opinion for PCT Application No. PCT/US2011/52976, mailed Jun. 1, 2012.

(Continued)

*Primary Examiner* — Tuan V Nguyen
(74) *Attorney, Agent, or Firm* — Vidas, Arrett & Steinkraus, P.A.

(57) ABSTRACT

An annuloplasty device includes a plurality of corkscrew anchors. The annuloplasty device further includes a core wire extending along the length of the device and at least one corkscrew wire which is operably connected to the corkscrew anchors to screw the corkscrew anchors into heart tissue. One or more of the corkscrew wires can include a drive key; the corkscrew anchors are connected to a sleeve with a keyway that engages the drive key on the corkscrew wires.

15 Claims, 8 Drawing Sheets

(56) References Cited

U.S. PATENT DOCUMENTS

| | | |
|---|---|---|
| 7,118,595 B2 | 10/2006 | Ryan et al. |
| 7,201,761 B2 | 4/2007 | Woolfson et al. |
| 7,296,577 B2 | 11/2007 | Lashinski et al. |
| 7,431,726 B2 | 10/2008 | Spence et al. |
| 7,635,386 B1 | 12/2009 | Gammie |
| 7,637,944 B2 | 12/2009 | Ryan et al. |
| 7,655,015 B2 | 2/2010 | Goldfarb et al. |
| 7,717,954 B2 | 5/2010 | Solem et al. |
| 2003/0078465 A1 | 4/2003 | Pai et al. |
| 2004/0148021 A1 | 7/2004 | Cartledge et al. |
| 2004/0215230 A1 | 10/2004 | Frazier et al. |
| 2004/0236419 A1 | 11/2004 | Milo |
| 2004/0243230 A1 | 12/2004 | Navia et al. |
| 2005/0065550 A1 | 3/2005 | Starksen et al. |
| 2005/0065601 A1 | 3/2005 | Lee et al. |
| 2005/0107812 A1 | 5/2005 | Starksen et al. |
| 2005/0137696 A1 | 6/2005 | Salahieh et al. |
| 2005/0222488 A1 | 10/2005 | Chang et al. |
| 2006/0276891 A1 | 12/2006 | Nieminen et al. |
| 2007/0027533 A1 | 2/2007 | Douk |
| 2007/0027536 A1 | 2/2007 | Mihaljevic et al. |
| 2007/0066993 A1 | 3/2007 | Kreidler |
| 2007/0080188 A1 | 4/2007 | Spence et al. |
| 2007/0112355 A1* | 5/2007 | Salahieh et al. ............ 606/108 |
| 2007/0112422 A1 | 5/2007 | Dehdashtian |
| 2007/0244556 A1 | 10/2007 | Rafiee et al. |
| 2007/0244557 A1 | 10/2007 | Rafiee et al. |
| 2008/0045977 A1 | 2/2008 | To et al. |
| 2008/0051840 A1 | 2/2008 | Moaddeb et al. |
| 2008/0065203 A1 | 3/2008 | Khalapyan |
| 2008/0262609 A1* | 10/2008 | Gross et al. ............... 623/2.36 |
| 2009/0177277 A1 | 7/2009 | Milo |
| 2010/0030014 A1 | 2/2010 | Ferrazzi |
| 2010/0121433 A1 | 5/2010 | Bolling et al. |
| 2010/0121435 A1 | 5/2010 | Subramanian et al. |
| 2010/0280604 A1 | 11/2010 | Zipory et al. |
| 2010/0324669 A1 | 12/2010 | Hlavka et al. |
| 2012/0123531 A1 | 5/2012 | Tsukashima et al. |

FOREIGN PATENT DOCUMENTS

| | | |
|---|---|---|
| WO | 2005055883 A1 | 6/2005 |
| WO | 2009/135022 | 11/2009 |
| WO | 2010091383 A2 | 8/2010 |
| WO | 2010091653 A1 | 8/2010 |

OTHER PUBLICATIONS

Search Report and Written Opinion for PCT Application No. PCT/US2012/030711, mailed Jun. 13, 2012.
Search Report and Written Opinion for PCT Application No. PCT/US2011/52865, mailed Jun. 13, 2012.
Amplatzer Multifenestrated Septal Occluder—"Cribriform", 2007-2010 AGA Medical Corporation, Plymouth, MN.
Amplatzer Septal Occluder and Delivery System, 2007-2010 AGA Medical Corporation, Plymouth, MN.
Simon Nitinol Filter Versatile and Dependable Performance, simon_vena_cava_filter.htm, Copyright 2004 C. R. Bard, Inc.
amplatzer_web_page_20101005.aspx.htm, viewed on Oct. 5, 2010.
U.S. Appl. No. 61/487,083 entitled "Annuloplasty Ring with Anchors Fixed by Curing Polymer," and filed May 17, 2011.
U.S. Appl. No. 61/487,053, entitled "Positioning Cage," and filed May 17, 2011.
U.S. Appl. No. 61/487,065, entitled "Percutaneous Mitral Annulus Mini-Plication," and filed May 17, 2011.
U.S. Appl. No. 61/487,072 "Annuloplasty Ring with Piercing Wire and Segmented Wire Lumen," and filed May 17, 2011.

* cited by examiner

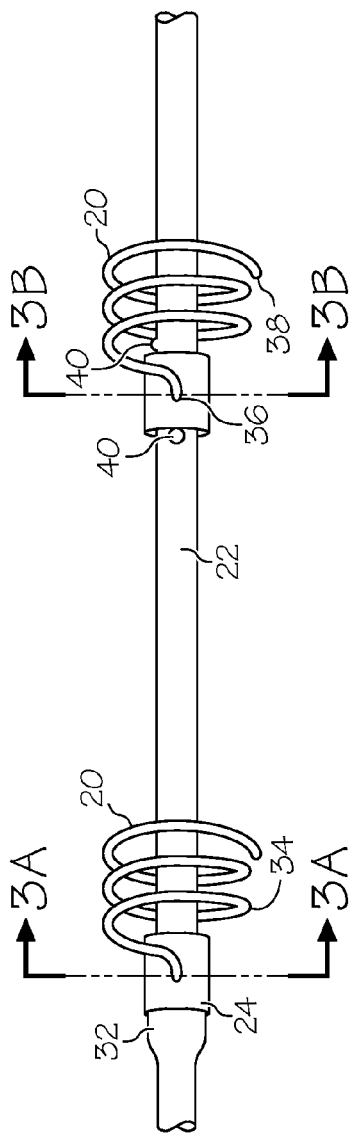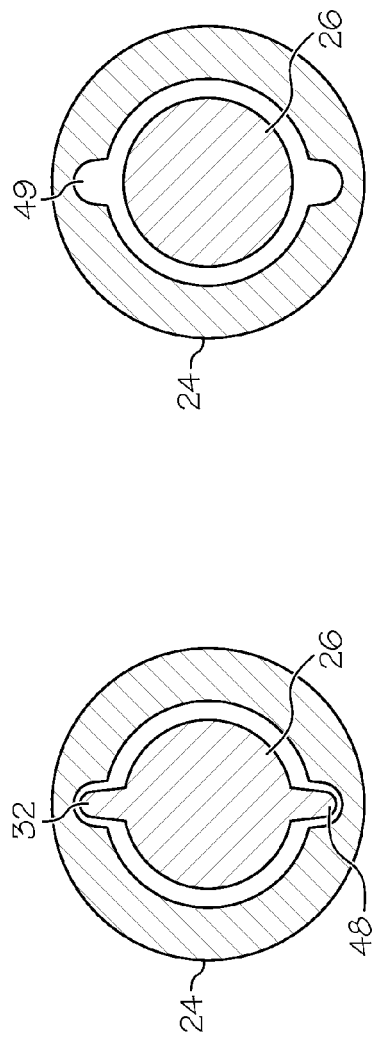

CORKSCREW ANNULOPLASTY DEVICE

CROSS-REFERENCE TO RELATED APPLICATIONS

This application claims priority to U.S. Application No. 61/487,063, filed on May 17, 2011, the entire contents of which are hereby incorporated by reference.

STATEMENT REGARDING FEDERALLY SPONSORED RESEARCH

Not Applicable.

FIELD OF THE INVENTION

The invention relates to an annuloplasty ring for repairing heart valves, and, in some embodiments, mitral valves.

BACKGROUND OF THE INVENTION

In an effort to stem the risk of heart valve disease, various medical procedures have been developed to repair or replace poorly functioning or stenosed heart valves. In particular, annuloplasty procedures have been used to repair heart valves by way of open heart surgery or, on a more limited basis, by way of less invasive techniques.

Mitral regurgitation is a particular type of heart valve disease wherein the mitral valve fails to sufficiently close, and blood is allowed to backflow across the valve. Consequently, many mitral annuloplasty procedures are designed to make the mitral annulus smaller, particularly in the septal—lateral dimension, allowing the mitral valve leaflets to coapt more effectively and preventing mitral regurgitation.

In some instances, repair of the mitral valve involves placing an annuloplasty ring on the mitral valve. Certain procedures involve suture-based cinching to reshape the mitral valve. In addition, some percutaneous annuloplasty procedures involve placing a rigid structure in the coronary sinus, which is near but not exactly at, the actual location of the mitral annulus. Such procedures can be cumbersome and may not be particularly effective or safe in all patients due to the anatomy of the coronary sinus, the mitral annulus, and the nearby circumflex coronary artery. In particular, coronary sinus devices may not be as effective as surgically placed devices, and crossing of the coronary sinus over the circumflex artery can cause dangerous compression of the artery by an annular cinching device placed in the coronary sinus.

Heretofore, reliable anchoring of an annuloplasty ring at a desirable location has been difficult using percutaneous and less invasive techniques. In addition, some prior attempts have utilized rather stiff structures in order to obtain the required shape and support for the valve. Consequently, there is a need for an annuloplasty procedure and device that overcomes the problems associated with prior approaches and devices.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In some embodiments, as discussed in more detail below, an annuloplasty device and method are provided for repairing a leaky heart valve, and in particular, a regurgitant mitral valve. In some embodiments, the annuloplasty device comprises an annuloplasty ring and the annuloplasty ring comprises at least one corkscrew anchor and at least one corkscrew wire. The at least one corkscrew anchor is deployed to attach to adjacent cardiac tissue, thereby anchoring the annuloplasty ring.

In some embodiments, the annuloplasty device comprises a core wire having a proximal end and a distal end, at least one corkscrew wire, and a plurality of corkscrew anchors. In some embodiments, each corkscrew anchor comprises a plurality of helical turns, the helical turns disposed around the core wire. In some embodiments, the annuloplasty device further comprises a looping wire; the looping wire is connected to the distal end of the core wire. Moreover, in some embodiments, the corkscrew anchors are selectively rotatably coupled to the corkscrew wire.

In some embodiments, the method of percutaneously implanting an annuloplasty device within a heart comprises providing an annuloplasty device within a deployment catheter. The annuloplasty device comprises a retractable sheath, a plurality of helical anchors, at least one torque wire operably connected to the helical anchors, a core wire, and a looping wire. The retractable sheath is disposed within the deployment catheter and exteriorly to the helical anchors. The method of percutaneously implanting an annuloplasty device within a heart further comprises extending the annuloplasty device out of the deployment catheter and at least partially retracting the retractable sheath to expose at least a portion of at least one of the helical anchors to adjacent heart tissue. In addition, the method of percutaneously implanting an annuloplasty device further comprises rotating the torque wire to penetrate the heart tissue with at least one of the helical anchors and securing the helical anchors to the adjacent heart tissue.

BRIEF DESCRIPTION OF THE SEVERAL VIEWS OF THE DRAWING(S)

FIG. 3 shows a partial view of a portion of an annuloplasty device.

FIGS. 3A and 3B show respective cross-sections of the annuloplasty device of FIG. 3.

DETAILED DESCRIPTION OF THE INVENTION

Figure 2:
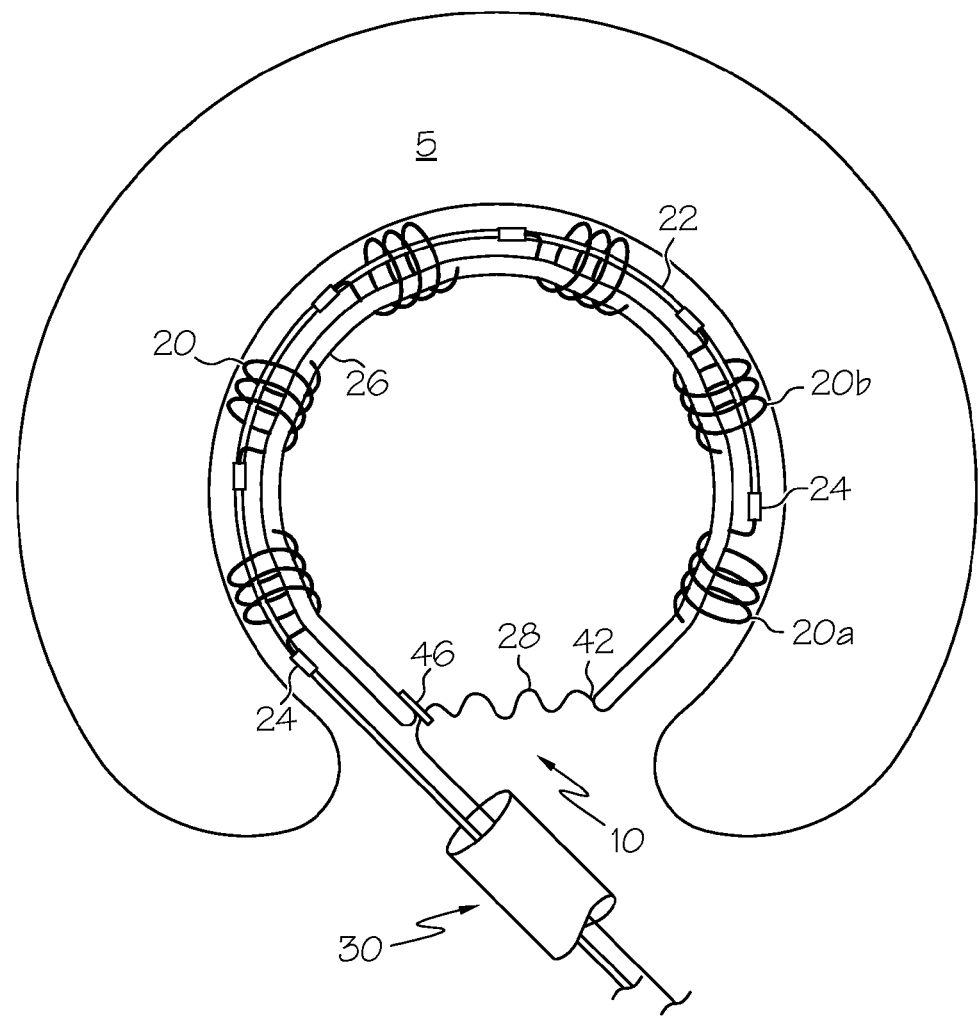
FIG. 2 shows a top view of the mitral annulus having an annuloplasty device partially attached thereto.

In at least one embodiment, an annuloplasty device 10 comprises a plurality of corkscrews 20, which are anchorable to adjacent heart tissue 5. In some embodiments, the annuloplasty device 10 further comprises a core wire 26 and a looping wire 28. Moreover, the annuloplasty device 10 comprises a proximal end 12 and a distal end 16. In some embodiments, the annuloplasty device 10 is inserted into the heart of a patient using a deployment catheter 30 (FIG. 2).

Figure 1:
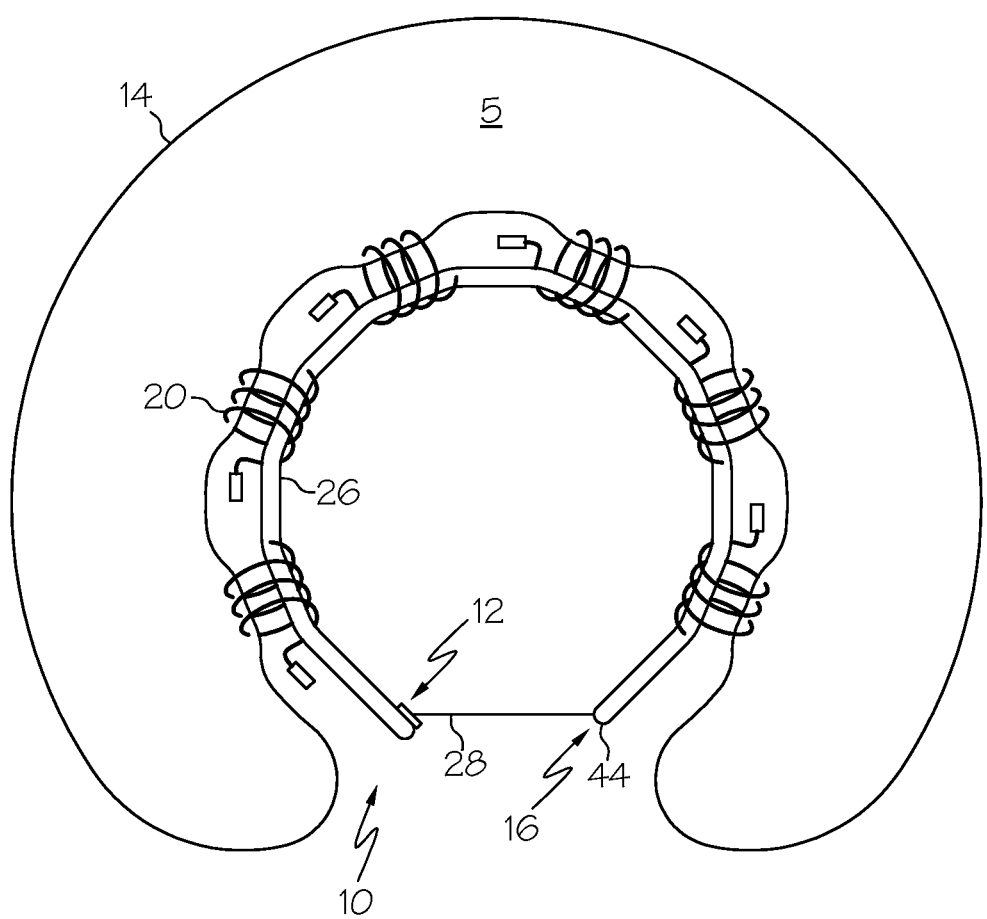
FIG. 1 shows a top view of the mitral annulus having an annuloplasty device attached thereto.

As shown in FIG. 1, an embodiment of the annuloplasty device 10 is anchored to adjacent heart tissue 5 by way of corkscrews 20. More particular, in some embodiments, the annuloplasty device 10 is anchored to the mitral annulus 14, with each of the corkscrews 20 being threaded through a portion of the annulus 14. With the corkscrews 20 anchored to the annulus 14, the annuloplasty device 10 is cinched, thereby reducing the size of the mitral valve, and reducing or eliminating regurgitation.

With further regard to FIG. 1, the annuloplasty device 10 is shown with a core wire 26. The core wire 26 is disposed through the lumen defined by the corkscrews 20. In addition, in some embodiments, the core wire 26 is cinched via looping wire 28. Cinching the core wire 26 pulls the corkscrews 20 and the adjacent heart tissue 5 together, thereby reducing the cross-section of the annulus 14.

Figure 6:
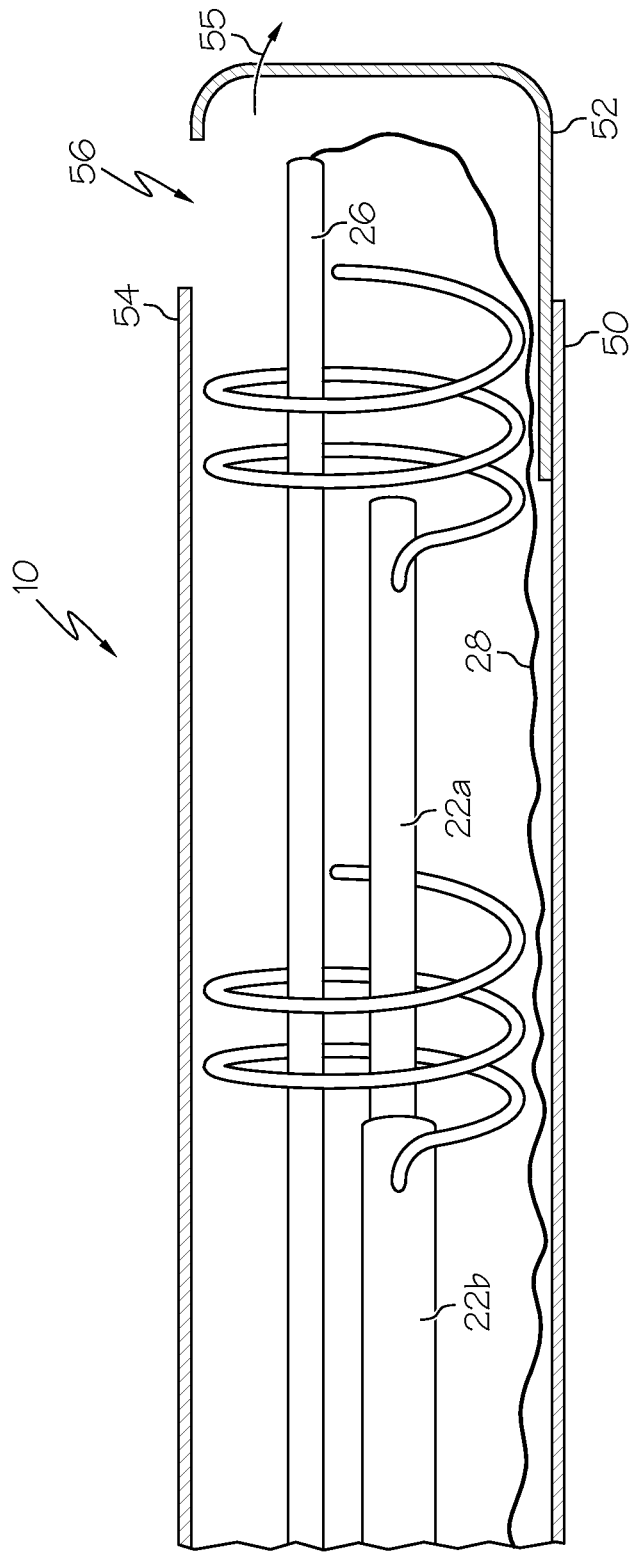
FIG. 6 shows a detailed view of the distal end of an annuloplasty device.

In some embodiments, the core wire 26 comprises a generally straight configuration, for example as shown in FIG. 6, during insertion of the annuloplasty device 10. Also, in some embodiments, the core wire 26 is biased to take on a predetermined shape, for example, a loop or partial loop, upon insertion of the annuloplasty device 10. In this way, in some embodiments, the core wire 26 supports the annuloplasty device 10. In some embodiments, the core wire 26 has a circular cross-section; the core wire 26 can also have any desirable cross-section, for example the core wire 26 can be flat or rectangular to bias the annuloplasty device 10 to stay in plane with the annulus. Also, in some embodiments, the core wire 26 is tubular and/or has a slotted tube configuration to provide limited bending flexibility in certain directions, while maintaining torsional stiffness. In some embodiments, the core wire 26 moves relative to one or both ends of the annuloplasty device 10 or corkscrews 20.

Turning to FIG. 2, in some embodiments, the annuloplasty device 10 comprises at least one corkscrew wire 22 extending along the length of the annuloplasty device 10. In some embodiments, the corkscrew wire 22 is rotatably coupled to one or more of the corkscrews 20. In particular, in the embodiment shown in FIG. 2, the corkscrews 20 are each attached to a sleeve 24 and the sleeves 24 are disposed over the corkscrew wire 22. In some embodiments, a portion of the corkscrew wire 22 selectively engages the sleeves 24 so that the sleeve(s) 24 can be selectively rotated by rotating the corkscrew wire 22. When engaged by the corkscrew wire 22, rotation thereof transmits torque to the sleeve 24 and the corkscrew 20. In this regard, a torque is applied to the proximal end of the corkscrew wire (not shown), which, in some embodiments, remains outside the patient's body during the procedure. Consequently, rotation of the proximal end of the corkscrew wire 22 anchors the corkscrews 20 in the heart tissue 5.

With further regard to FIG. 2, the looping wire 28 is shown in a relaxed configuration. In some embodiments, the looping wire 28 is pulled taught after all of the corkscrews 20 are anchored to the heart tissue 5, encouraging coaptation of the valve.

More particularly, referring to FIGS. 3, 3A, and 3B, in some embodiments, each corkscrew 20 is rotated independently of the other corkscrews. In particular, in some embodiments, the corkscrew wire 22 comprises a drive key 32 which is configured to engage the sleeve 24. Moreover, in some embodiments, the core wire 26 is slidable within the sleeves 24 so that the drive key 32 engages each of the sleeves 24 independently. More specifically, in some embodiments, the drive key 32 is positioned within one of the sleeves 24 and the corkscrew wire 22 is rotated until the corresponding corkscrew 20 is anchored in adjacent heart tissue 5. For example, as shown in FIG. 2, the drive key 32 is shown as engaging the sleeve 24 of the distal most corkscrew 20a; the distal most corkscrew 20a is screwed into the adjacent heart tissue 5. Subsequently, the corkscrew wire 22 is repositioned proximally so that the drive key 32 engages the sleeve 24 of the next corkscrew 20b. Then the corkscrew wire 22 is again rotated until the corresponding corkscrew 20b is anchored in adjacent hear tissue 5. This process is repeated until all of the corkscrews 20 are anchored as desired.

In some embodiments, the drive key 32 is disposed at or near the distal end of the corkscrew wire 22. Alternatively, in some embodiments, the drive key 32 is disposed along a portion of the corkscrew wire 22 that is initially aligned with the proximal most corkscrew 20. In some embodiments, the proximal most corkscrew 20 is threaded into heart tissue first. The drive key 32 can also be disposed along any desirably portion of the corkscrew wire 22.

In some embodiments, the drive key 32 comprises two lobes 48 which selectively engage the recesses 49 or keyways of the sleeve 24. In some embodiments, the drive key 32 comprises only a single lobe 48. Alternatively, in some embodiments, the corkscrew wire 22 comprises a spline or other geometrical shape that can selectively engage the sleeve 24.

Additional engagement features can be incorporated to hold the corkscrews 20 that are not being rotated in place while rotating the corkscrew 20 that is being threaded into adjacent heart tissue 5. Engagement features include, for example, magnetic or electromagnetic interface elements, an interference fit, bumps or detents, actuated pins or keys, releasable sleeves, additional wires, and the like. The engagement features can serially disengage upon securement of each corkscrew 20 into adjacent heart tissue.

For example, in some embodiments, the corkscrew wire 22 comprises a plurality of projections 40. In some embodiments, the projections 40 are bumps or raised portions positioned on one or both sides of one or more of the sleeves 24 when the drive key 32 is aligned with one of the sleeves 24. The projections 40 maintain the position of the sleeves 24 along a particular length of the corkscrew wire 22 by preventing inadvertent sliding of the sleeve 24 over the corkscrew wire 22. The projections 40 bump up against the sleeve 24 to keep the sleeve 24 in a desired position along the length of the corkscrew 20 until the corkscrew wire 22 is desirably repositioned to engage a subsequent sleeve 24. When the drive key 32 is to be repositioned, the projections 40 can slide through the sleeve 24 with the application of additional force, such as when subsequently cinching the mitral annulus 14.

Alternatively to the projections 40, or in addition thereto, in some embodiments, the corkscrew wire 22 has a varying cross-sectional area along its length. In some embodiments, the corkscrew wire 22 has an enlarged cross-section or reduced cross-section along one or more portions of its length. In some embodiments, the portion(s) having enlarged or reduced cross-sections matingly engage a sleeve 24 to keep the sleeve 24 at the particular location along the corkscrew wire 22. Also, in some embodiments, the corkscrew wire 22 includes one or more magnets disposed along its length. The one or more ring magnets are used at each sleeve 24, and each keyway sleeve includes a corresponding ring magnet to prevent the sleeves 24 from inadvertently sliding along the corkscrew wire 22. When the corkscrew wire 22 is desirably moved with respect to the sleeve(s) 24, the corresponding magnets' interaction can be broken, and the corkscrew wire 22 is repositioned with respect to the sleeve 24.

Turning now to the corkscrews 20, in some embodiments, the corkscrews 20 comprise a plurality of helical turns 34, for example 2-10 turns. Moreover, in some embodiments, the corkscrews 20 are anchored at a first end 36 to the sleeve 24, while the second end 38 has a piercing tip to puncture the heart tissue 5. In some embodiments, for example as shown in FIG. 3, the piercing tip of the second end 38 extends outwardly (radially) beyond the remaining turns 34 of the corkscrew to effectively bite into the tissue 5 without the remaining turns 34 interfering with the tissue 5. In some embodiments, the corkscrews 20 comprise stainless steel. Alternatively, the corkscrews 20 comprise a NiTi alloy (e.g., Nitinol), or other superelastic material, platinum, or any other suitable metal or material. In addition, in some embodiments, the corkscrews 20 comprise a material that is porous or has a rough surface, in order to encourage tissue fixation, further preventing the corkscrews 20 from backing out of the tissue 5.

Returning to FIG. 2, in some embodiments, the looping wire 28 comprises a first end (not shown), which is disposed outside the patient's body, and a second end 42. In some embodiments, the second end 42 is attached to the distal end 44 of the core wire 26. Further, in some embodiments, the looping wire 28 extends through a wire lock 46 and the catheter 30.

In some embodiments, the wire lock 46 comprises a ratcheting mechanism or a spring-loaded latch. Alternatively, or in addition thereto, in some embodiments, the wire lock 46 includes a wedge that is driven between the looping wire 28 and a wall of the wire lock, thereby securing the looping wire 28 to the wire lock 46. In some embodiments, the wedge comprises a cylindrical taper or collet through which the looping wire 28 is fed. Then, the cylindrical taper or collet is inserted into a housing of the wire lock 46 to secure the looping wire 28. In some embodiments, the wire lock 46 comprises a deformable portion that is plastically deformed to secure the looping wire 28. And, in some embodiments, the looping wire 28 is thermally or chemically bonded to the wire lock 46.

Figure 4:
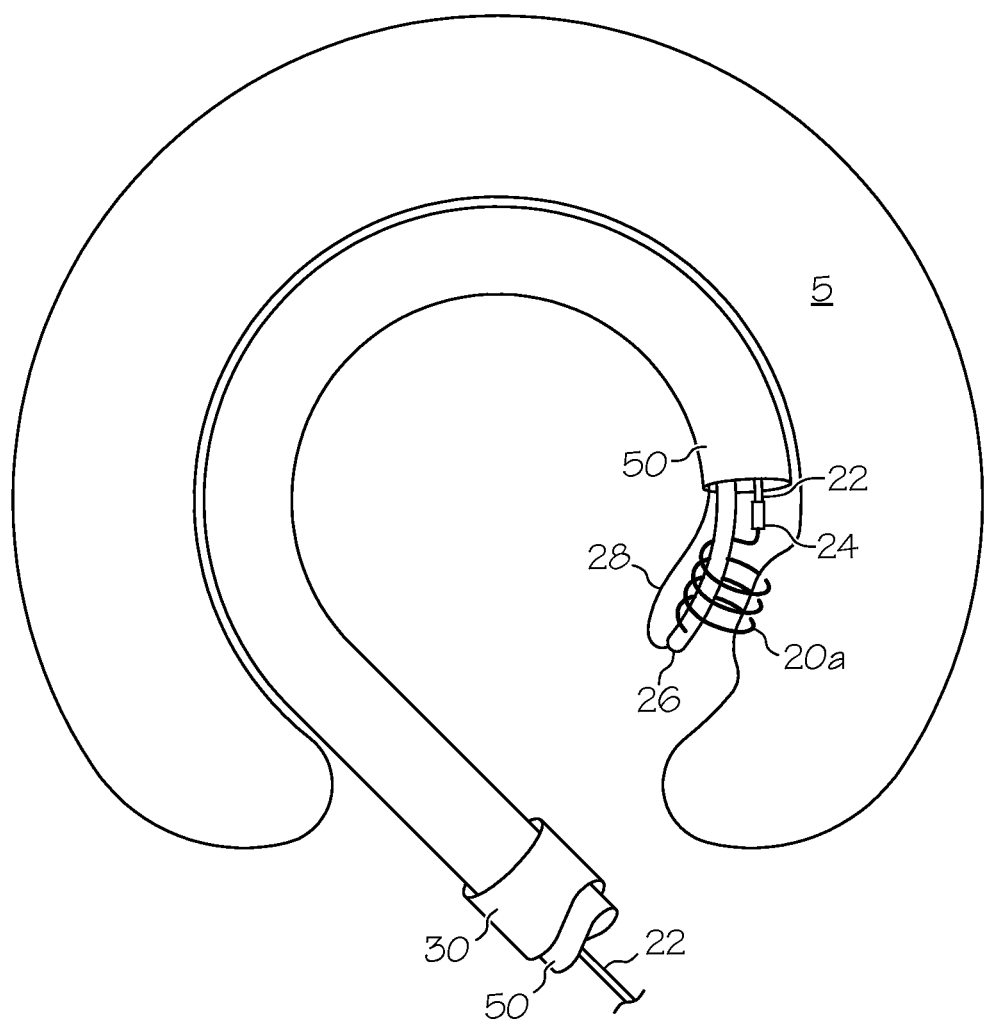
FIG. 4 shows a top view of an annuloplasty device being inserted into the mitral annulus.

Turning to FIG. 4, in some embodiments, the annuloplasty device 10 comprises a retractable sheath 50. As shown in FIG. 3, the retractable sheath 50 has been retracted to reveal the distal most corkscrew 20a. Moreover, the distal most corkscrew 20a has been threaded through the adjacent heart tissue 5 of the mitral annulus 14 by way of corkscrew wire 22. In some embodiments, the retractable sheath 50 covers all of the corkscrews 20 during insertion of the annuloplasty device 10. After the annuloplasty device 10 has been located at or near its desired destination the retractable sheath 50 is retracted. In some embodiments, the retractable sheath 50 is retracted from the annuloplasty device 10 in stages. For example, in some embodiments, the retractable sheath 50 is retracted to reveal the distal most corkscrew 20a first. Subsequently, the distal most corkscrew 20a is inserted into the adjacent heart tissue 5 by rotation of the corkscrew wire 22. Thereafter, the retractable sheath 50 is retracted to reveal the next corkscrew (20b in FIG. 2). Then, the corkscrew wire 22 is repositioned to engage the next corkscrew (20b in FIG. 2), after which the corkscrew wire 22 is rotated to insert the helical turns 34 of the corkscrew into the adjacent heart tissue 5. This procedure is repeated until all of the corkscrews 20 are attached to the heart tissue 5.

In some embodiments, the retractable sheath 50 is straight prior to implantation. The retractable sheath 50 is in a straight configuration during introduction and advancement through the patient's vasculature. Moreover, in some embodiments, the retractable sheath 50 is biased in the straight configuration, for example, to counteract a looping bias of the core wire 26. Alternatively, in some embodiments, the annuloplasty device 10 comprises a plurality of control wires, which are configured to hold the annuloplasty device 10 straight during insertion.

Figure 5:
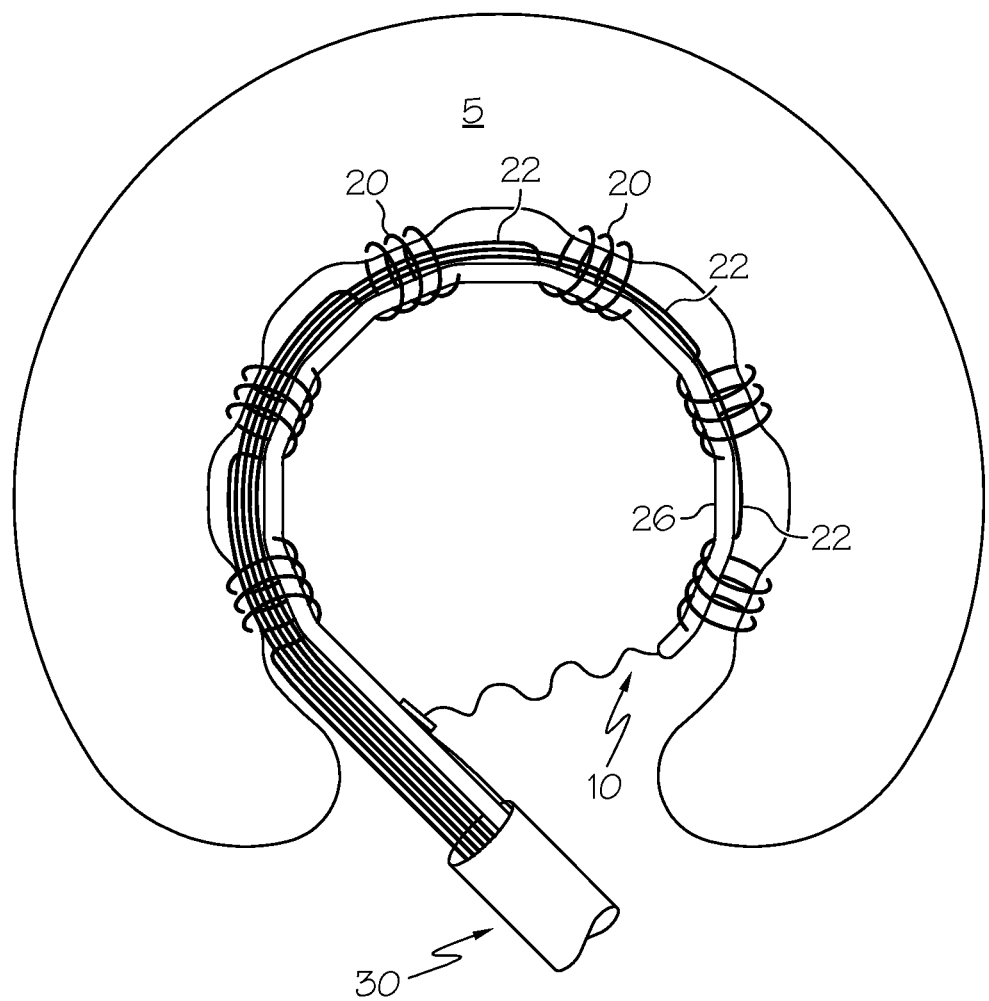
FIG. 5 shows a top view of annuloplasty device having a plurality of corkscrew wires.

In some embodiments, for example as shown in FIG. 5, the annuloplasty device 10 comprises a plurality of corkscrew wires 22. As shown in FIG. 5, each corkscrew wire 22 is attached to a single corkscrew 20. In this way, each of the corkscrews 20 is anchored to the adjacent heart tissue 5 by rotation of the respective corkscrew wire 22. In some embodiments, each of the corkscrew wires 22 is attached to a corkscrew 20 at a distal end of the respective corkscrew wire 22. In some embodiments, the corkscrew wires 22 are detachable from the corkscrews 20 such that the corkscrew wires 22 can be detached from the corkscrews 20 after the corkscrews 20 are secured to the heart tissue 5.

In some embodiments, the annuloplasty device 10 further comprises a nosecone 52 attached to a distal end 54 of the retractable sheath 50, for example as shown in FIG. 6. In some embodiments, the nosecone 52 shields the components inside the retractable sheath 50 from interference or entanglement with tissue or other structures through which the annuloplasty device 10 can be inserted. For example, in some embodiments, the annuloplasty device is implanted using the "Positioning Cage" disclosed in the application of the same name, having Application No. 61/487,053, filed May 17, 2011, which is herein incorporated by reference. In some embodiments, the nosecone 52 is attached to the retractable sheath 50 along only a portion of the distal end 54 of the retractable sheath 50. In this way, in some embodiments, the nosecone 52 flexes, as shown by arrow 55, as the retractable sheath 50 is retracted. The nosecone 52 comprises a metal shield or wire cage, or, in some embodiments, a polymeric extension of the retractable sheath 50. The nosecone 52 can comprise an integral portion of the retractable sheath 50 or, in some embodiments, the nosecone 52 is a separate structure. Also, in some embodiments, the nosecone 52 is attached to the core wire 26 or corkscrew wire 22. Further, where the nosecone 52 is attached to a corkscrew wire 22, in some embodiments, the corkscrew wire 22 is permitted to rotate relative to the nosecone 52.

In some embodiments, the nosecone 52 is attached to the retractable sheath 50 along an entire perimeter of the distal end 54 of the retractable sheath 50. In order to permit the nosecone 52 to pass over the corkscrews 20 (and other components), in some embodiments, the nosecone 52 comprises a plurality of slits. As the retractable sheath 50 is retracted, the nosecone 52 splits apart at the slits, permitting the nosecone 52 to pass over the various components of the annuloplasty device 10. In some embodiments, the nosecone 52 comprises a zipper that is pulled back as the nosecone 52 is retracted.

In some embodiments, the nosecone 52 has one or more outrigger tabs attached thereto. The outrigger tab is a projection extending radially outwardly from the nosecone. In some embodiments, the nosecone 52 includes two outrigger tabs attached thereto, the outrigger tabs are on opposite sides of the nosecone and are positioned to be forced against the tissue of the vasculature through which the annuloplasty device 10 is being inserted. In this way, the outrigger tabs prevent the nosecone 52 from rotating as the annuloplasty device 10 is inserted into the patient.

With additional reference to FIG. 6, in some embodiments the corkscrews 20 are attached to concentric corkscrew wires 22a, 22b. Each of the concentric corkscrew wires 22a, 22b, is able to be rotated independently of the remaining corkscrew wires such that a desired corkscrew 20 can be threaded into adjacent heart tissue without manipulation of the remaining corkscrews 20. Moreover, in some embodiments, the concentric corkscrew wire 22b comprises a hollow tube through which concentric corkscrew wire 22a passes. Although not shown in FIG. 6, in some embodiments, the corkscrew wire 22b passes through an additional concentric corkscrew wire, which is also tubular. An additional concentric corkscrew wire is added with each additional corkscrew 20 and the concentric corkscrew wires distal to the more proximal corkscrew wires pass through the more proximal corkscrew wires, in the fashion shown in FIG. 6.

Alternatively, in some embodiments, the annuloplasty device 10 comprises two or more sets of concentric corkscrew wires 22a, 22b. For example, in some embodiments where the annuloplasty device 10 comprises six corkscrews 20, the annuloplasty device 10 comprises two sets of concentric corkscrew wires. Each set of concentric corkscrew wires consists of three concentric wires, for example, in the fashion shown in FIG. 6. And, for example, the first set of concentric corkscrew wires is attached to the proximal three most corkscrews 20, each of the three wires attached to a single corkscrew 20, while the second set of three concentric corkscrew wires is attached to the distal three most corkscrews, each of the three wires attached to a single corkscrew 20. Other embodiments are also possible, for example three sets of concentric corkscrew wires, each set having two concentric wires, etc. Also, the annuloplasty device 10 can comprise any desirable number of corkscrews 20, for example 2-10 corkscrews.

In some embodiments, the looping wire 28 is disposed within the retractable sheath 50 during insertion of the annuloplasty device 10. And, in some embodiments, the looping wire 28 is disposed exteriorly to the corkscrews 20 but interiorly to the retractable sheath 50. After the retractable sheath 50 is retracted, the looping wire 28 can be pulled to cinch the annulus.

Alternatively, in some embodiments, the looping wire 28 is disposed outside the retractable sheath 50. In this case, in some embodiments, the looping wire 28 passes through the opening 56 between the nosecone 52 and the retractable sheath 50. In addition, in some embodiments, the retractable sheath 50 has a tear line along the length of the sheath 50. As the retractable sheath 50 is retracted, the looping wire 28, outside the sheath, cuts through the tear line to permit retraction of the retractable sheath 50. Also, one particular advantage of having the looping wire 28 outside the retractable sheath 50 is to prevent entanglement of the looping wire 28 with the corkscrews 20. In contrast, however, an advantage of having the looping wire 28 disposed within the retractable sheath 50 is that the looping wire 28 is less likely to get hung up on the patient's vasculature or any structure outside the retractable sheath 50 during insertion of the annuloplasty device 10.

In some embodiments, the core wire 26 and corkscrew wire 22 are concentric. For example, in some embodiments, the corkscrew wire 22 comprises a tubular sleeve or lumen through which the core wire 26 extends. In this regard, the corkscrew wire 22 can function as discussed in the various embodiments. More particularly, where the core wire 26 is disposed through the corkscrew wire 22, after the corkscrews 20 are anchored and the corkscrew wire 22 is withdrawn, the core wire 26 remains threaded through the sleeves 24 attached to the corkscrews 20.

Further, in some embodiments, the corkscrew wire 22 comprises a slotted tube or helical torque wire. The corkscrew wire 22 comprising a helical torque wire has multiple wires that are wrapped together in a helical fashion.

Figure 7:
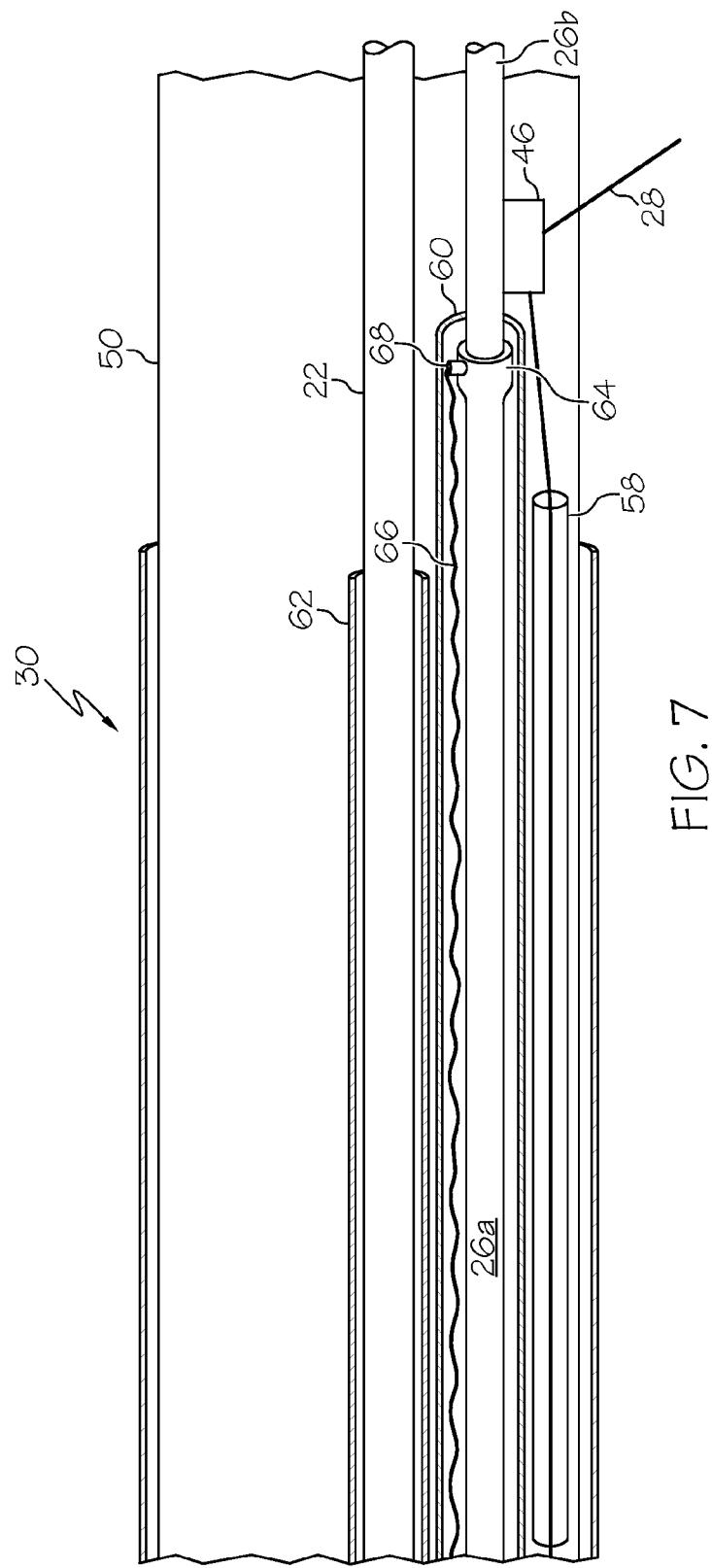
FIG. 7 shows a detailed view of a portion of the annuloplasty device.

Turning to FIG. 7, in some embodiments, the annuloplasty device 10 comprises a looping wire sheath 58, a detachment control sheath 60, and a corkscrew wire sheath 62. The looping wire 28 is disposed within the looping wire sheath 58. In some embodiments, the catheter 30 and the looping wire sheath 58 are coterminous, or approximately coterminous, such that the distal ends of the catheter 30 and the looping wire sheath 58 extend longitudinally to the same extent. During surgery, the proximal end of the looping wire 28 extends outside of the patient's body so it can be manipulated and the annuloplasty device 10 can be cinched together. After cinching, in some embodiments, the looping wire 28 is severed or detached proximally to the wire lock 46. In some embodiments, the looping wire 28 is detached by way of electrolytic separation, a GDC (Guglielmi Detachable Coil), releasable connector(s), screw connection, thermal melting, looped suture pull-out, pull wire or pin, shearing, or any other desired separation mechanism.

In some embodiments, the detachment control sheath 60 has at least a portion of the core wire 26 disposed therein. In some embodiments, the catheter 30 and the detachment control sheath 60 are coterminous, or approximately coterminous, such that the distal ends of the catheter 30 and the detachment control sheath 60 extend longitudinally to the same extent. In some embodiments, the core wire 26 comprises a coupler 64. The coupler 64 connects two segments of the core wire 26. In this regard, in some embodiments, after the annuloplasty device 10 is inserted and anchored to adjacent heart tissue 5, the proximal segment 26a of the core wire can be removed, while the distal segment 26b remains in the patient's body. In some embodiments, the proximal segment 26a of the core wire detached from the distal segment 26b of the core wire by way of a pull wire 66 and pin 68. The pull wire 66 extends proximally out through the detachment control sheath 60 and catheter 30 such that it can be pulled after the annuloplasty device is secured to heart tissue 5. Then, the pull wire 66 is pulled to release the pin 68, detaching the proximal segment 26a from the distal segment 26b of the core wire. In some embodiments, the core wire 26 is detached by way of a releasable connector latch, electrolytic separation, shearing or severing of the core wire 26, screw connection, thermal melting, looped suture pull-out, or any other suitable manner.

In some embodiments, the corkscrew wire 22 has a corkscrew wire sheath 62 disposed around at least a portion of corkscrew wire 22. In some embodiments, the distal end of the corkscrew wire sheath 62 is coterminous, or approximately coterminous, with the distal end of the catheter 30. In some embodiments, for example where multiple corkscrew wires 22 are used, the catheter 30 comprises a plurality of corkscrew wire sheaths 62. The corkscrew wires 22 are permitted to rotate and move within the corkscrew wire sheath 62. And, upon anchoring of the corkscrews 20 to the heart tissue 5, in some embodiments, the corkscrew wire(s) 22 are removed from the patient's body.

Figure 8:
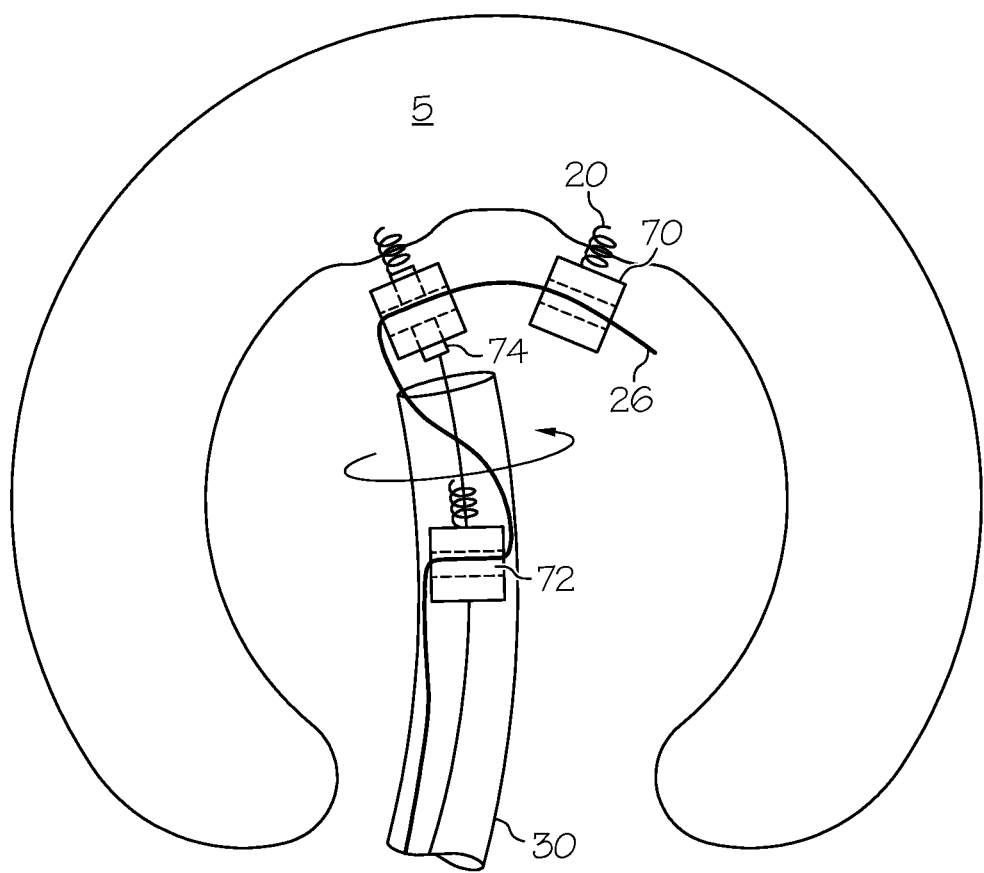
FIG. 8 shows a top view of the mitral annulus having an annuloplasty device partially attached thereto.

As shown in FIG. 8, in some embodiments, the longitude of the corkscrews 20 is generally perpendicular to the mitral annulus 14. As further shown in FIG. 8, in some embodiments, the corkscrews 20 are delivered via a catheter 30, which is articulated. The catheter 30 is repositioned to screw each of the corkscrews 20 into adjacent heart tissue 5. In some embodiments, a corkscrew sleeve 70 is rotatably attached to each corkscrew 20. The corkscrew sleeve 70 has an opening 72 through which the core wire 26 passes, allowing the core wire 26 to cinch the assembly. In some embodiments, the core wire 26 doubles as the looping wire 28. In some embodiments, the looping wire 28 is not used, and the core wire 26 cinches the heart tissue 5 together to reduce the size of the annulus.

In some embodiments, the corkscrews 20 are rotated via a driver 74 that engages a portion of the corkscrew 20 to rotate the corkscrew into the heart tissue 5. The corkscrew sleeve 70 has an outer race within which a bearing resides such that the sleeve 70 does not rotate with the corkscrew 20 as the corkscrew is rotated. In this way, the driver 74 engages an inner race that is connected to the corkscrew 20. In some embodiments, the inner race has a keyway and the driver has a matching key. In some embodiments, the driver is geared.

In some embodiments, the catheter 30, shown in FIG. 8, comprises a concentric shaft and tube. In some embodiments, the shaft is actuatably deflected to direct the distal end of the catheter to the desired spot on the mitral annulus 14, while the concentric tube is rotated to drive in the corkscrew 20. Each corkscrew 20 is engaged in sequence. The corkscrews 20 that have not yet been screwed into heart tissue 5 freely rotate with respect to the shaft. Alternatively, the roles of the concentric shaft and tube can be reversed such that the shaft is rotated to drive in the corkscrews 20.

In some embodiments, the annuloplasty device 10 is inserted from a retrograde arterial access or trans-septal access, or a combination of both. In some embodiments, for example where the annuloplasty device 10 is positioned for intracardiac deployment, the annuloplasty device 10 is used in combination with a guidewire and/or navigation sheath. In some embodiments, the guidewire and/or navigation sheath is inserted via a femoral vein access. After the guidewire and/or navigation sheath are in place, in some embodiments, the annuloplasty device 10 is inserted over the guidewire and/or within the navigation sheath, crossing the atrial septum, to reach the atrial side of the mitral annulus. After this, the annuloplasty device 10 is positioned at the mitral annulus 14. Subsequently, the guidewire and/or navigation sheath are retracted, followed, in some embodiments, by the retractable sheath 50. Then, the corkscrews 20 are inserted into the adjacent heart tissue 5 of the mitral annulus 14. After this, the core wire 26 is cinched by way of the looping wire 28, after which the looping wire 28 is detached, along with the core wire 26; the corkscrew wire 22 is removed.

In some embodiments, the annuloplasty device 10 is inserted via a minimally invasive thoracotomy or pericardial approach for epicardial deployment. In this respect, in some embodiments, the annuloplasty device 10 does not include a looping wire 28. Instead, in some embodiments, the core wire 26 comprises a cinch lock. More particularly, when the annuloplasty device 10 is deployed epicardially, it may be difficult to get a complete circumferential cinch. As such, in some embodiments, the individual corkscrews 20 are inserted into adjacent heart, pushed together, and secured to the core wire 26 after being pushed together. Moreover, in some embodiments, only the proximal most corkscrew 20 is pushed distally along the core wire 26 (after it has been threaded in to heart tissue) and secured to the core wire 26 to hold it in place. In some embodiments, one or more of the corkscrews 20 is secured to the core wire 26 by way of a cinch lock, which maintains the annuloplasty device 10 in a reduced dimension, thereby enhancing heart valve performance and reducing or eliminating regurgitation.

In some embodiments, corkscrew wires 22 and/or core wire 26 comprise a metal material, for example, stainless steel, nickel-titanium alloy (e.g., Nitinol), platinum, or any other suitable metal or metal alloy. In addition, in some embodiments, the corkscrew wires 22 and/or core wire 26 comprise polymeric material, for example polyethylene terephthalate (PET), sold under the trade name Dacron®. And, in some embodiments, the corkscrew wires 22 and/or core wire 26 comprise metallic braid reinforced polymeric material. Also, in some embodiments, the annuloplasty device 10 includes a thrombosis-modifying or healing coating on any or all of the components, for example corkscrews 20.

Although particular features are shown or described with respect to particular embodiments disclosed herein, it will be appreciated that these features can be combined with the features or substituted for the features of other embodiments.

In addition, the applications entitled "Percutaneous Mitral Annulus Mini-Plication," with Application No. 61/487,065 (corresponding utility application published as Pub. No. 2012/0296349), "Positioning Cage," with Application No. 61/487,053 (corresponding utility application published as Pub. No. 2012/0296160), "Annuloplasty Ring with Piercing Wire and Segmented Wire Lumen," with Application No. 61/487,072 (corresponding utility application published as Pub. No. 2012/0296420), and "Annuloplasty Ring with Anchors Fixed by Curing Polymer," with Application No. 61/487,083 (corresponding utility application published as Pub. No. 2012/0296419), all of which were filed on May 17, 2011, the contents of which are hereby incorporated by reference. In particular, certain features shown and described in these applications (and those incorporated by reference elsewhere) can be incorporated into the annuloplasty device of the immediate application. Moreover, in some embodiments, the Positioning Cage of the application by the same name is used to perform implantation of the annuloplasty device of the immediate application.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to." Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. An annuloplasty device comprising:
   a core wire having a distal end;
   at least one corkscrew wire;
   a plurality of corkscrew anchors disposed around the core wire, each corkscrew anchor comprising a plurality of helical turns, the helical turns defining a lumen therethrough, the core wire extending through the lumen and along the length of the lumen; and
   a looping wire, the looping wire connected to the distal end of the core wire;
   at least one of the corkscrew anchors rotatably coupled to the at least one corkscrew wire such that rotation of the at least one corkscrew wire rotates at least one of the corkscrew anchors.

2. The annuloplasty device of claim 1 further comprising a retractable sheath, at least a portion of the retractable sheath disposed over the plurality of corkscrew anchors.

3. The annuloplasty device of claim 2, wherein the retractable sheath comprises a distal end and the annuloplasty device further comprising a nosecone, the nosecone attached to the distal end of the retractable sheath.

4. The annuloplasty device of claim 1, wherein the at least one corkscrew wire comprises a drive key.

5. The annuloplasty device of claim 4, wherein the drive key comprises at least one lobe.

6. The annuloplasty device of claim 5 further comprising a plurality of keyway sleeves, each keyway sleeve attached to a corkscrew anchor, each keyway sleeve having at least one recess, the at least one lobe of the drive key selectively engageable with the at least one recess.

7. The annuloplasty device of claim 1, wherein the core wire further comprises a proximal end, the looping wire extending from the distal end to the proximal end.

8. The annuloplasty device of claim 7 further comprising a wire lock, the wire lock attached to the proximal end of the core wire and the looping wire captured by the wire lock.

9. The annuloplasty device of claim 8 further comprising a retractable sheath, the looping wire disposed within the retractable sheath.

10. The annuloplasty device of claim 9, wherein the looping wire is disposed exteriorly to the corkscrew anchors.

11. A method of percutaneously implanting an annuloplasty device via a deployment catheter within a heart, the method comprising:
   providing an annuloplasty device comprising:
      a catheter having a retractable sheath, a plurality of helical anchors, at least one torque wire connected to the helical anchors, and a core wire, the retractable sheath disposed exteriorly to the helical anchors, the helical anchors each comprising a plurality of helical turns defining a lumen, the core wire extending through the lumen and along the length of the lumen;
   extending the annuloplasty device out of the deployment catheter;
   at least partially retracting the retractable sheath to expose at least a portion of at least one of the helical anchors to adjacent heart tissue;
   rotating the at least one torque wire thereby penetrating the heart tissue with at least one of the helical anchors; and
   securing the helical anchors to the adjacent heart tissue.

12. The method of claim 11, wherein the step of securing the helical anchors to the adjacent heart tissue comprises securing each of the helical anchors to adjacent heart tissue one-at-a-time.

13. The method of claim 11, wherein the step of securing the helical anchors to the adjacent heart tissue comprises securing all of the helical anchors to the adjacent heart tissue simultaneously.

14. An annuloplasty device comprising:
   a core wire having a proximal end and a distal end;
   a plurality of corkscrew wires;
   a plurality of corkscrew anchors disposed around the core wire, each corkscrew anchor comprising a plurality of helical turns, the helical turns defining a lumen therethrough, the core wire extending through the lumen and along the length of the lumen; and
   a looping wire, the looping wire connected to the proximal and distal ends of the core wire;
   each of the corkscrew anchors attached to a single corkscrew wire.

15. The annuloplasty device of claim 14, wherein the looping wire comprises a severable connection.

* * * * *